United States Patent
Ide et al.

(10) Patent No.: US 9,863,955 B2
(45) Date of Patent: Jan. 9, 2018

(54) AMPK ACTIVATOR SCREENING METHOD, AND AMPK ACTIVATOR

(71) Applicant: KYORIN PHARMACEUTICAL CO., LTD., Tokyo (JP)

(72) Inventors: Tomohiro Ide, Nogi-machi (JP); Naoki Kobayashi, Nogi-machi (JP); Yunike Akasaka, Nogi-machi (JP); Takashi Komine, Nogi-machi (JP); Koji Murakami, Nogi-machi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 546 days.

(21) Appl. No.: 14/400,945

(22) PCT Filed: May 16, 2013

(86) PCT No.: PCT/JP2013/063689
§ 371 (c)(1),
(2) Date: Nov. 13, 2014

(87) PCT Pub. No.: WO2013/172421
PCT Pub. Date: Nov. 21, 2013

(65) Prior Publication Data
US 2015/0126387 A1    May 7, 2015

(30) Foreign Application Priority Data

May 17, 2012  (JP) .................. 2012-113424

(51) Int. Cl.
*G01N 33/68*   (2006.01)
*A61K 45/00*   (2006.01)
(Continued)

(52) U.S. Cl.
CPC ......... *G01N 33/6845* (2013.01); *A61K 45/00* (2013.01); *C12N 9/12* (2013.01);
(Continued)

(58) Field of Classification Search
CPC .. G01N 33/6848; G01N 33/573; G01N 33/68; G01N 2333/4703; G01N 2333/912;
(Continued)

(56) References Cited

U.S. PATENT DOCUMENTS

2010/0069462 A1   3/2010  Endo et al.
2010/0160428 A1   6/2010  Cooper et al.
(Continued)

FOREIGN PATENT DOCUMENTS

CN    101843903    9/2010
EP    0 578 909    1/1994
(Continued)

OTHER PUBLICATIONS

International Preliminary Report on Patentability and Written Opinion dated Nov. 18, 2014 in International (PCT) Application No. PCT/JP2013/063689.
(Continued)

*Primary Examiner* — Jeremy C Flinders
(74) *Attorney, Agent, or Firm* — Wenderoth, Lind & Ponack, L.L.P.

(57) ABSTRACT

A method for screening an AMPK activator, wherein inhibition of an interaction between prohibitin and AMPK is used as an index is provided. Besides, an AMPK activator comprising, as an active ingredient, a compound inhibiting an interaction between prohibitin and AMPK, and a prohibitin-AMPK complex are also provided.

10 Claims, 8 Drawing Sheets

(a)

(b)

(51) Int. Cl.
    C12N 9/12      (2006.01)
    C12Q 1/48      (2006.01)
    G01N 33/573    (2006.01)
    C07K 14/47     (2006.01)
    C12N 15/113    (2010.01)

(52) U.S. Cl.
    CPC ...... *C12Q 1/485* (2013.01); *C12Y 207/11031* (2013.01); *G01N 33/573* (2013.01); *G01N 33/68* (2013.01); *C07K 14/4703* (2013.01); *C12N 15/113* (2013.01); *C12N 2310/14* (2013.01); *G01N 2333/4703* (2013.01); *G01N 2333/912* (2013.01); *G01N 2500/02* (2013.01)

(58) Field of Classification Search
    CPC ...... G01N 2500/02; C12Q 1/485; C12N 9/12; C12N 2310/14; C12N 15/113; C12Y 207/11031; A61K 45/00; C07K 14/4703
    See application file for complete search history.

(56) References Cited

U.S. PATENT DOCUMENTS

| | | |
|---|---|---|
| 2012/0196298 A1 | 8/2012 | Endo et al. |
| 2012/0202215 A1 | 8/2012 | Endo et al. |
| 2013/0108709 A1 | 5/2013 | Cooper et al. |

FOREIGN PATENT DOCUMENTS

| | | |
|---|---|---|
| JP | 5-271294 | 10/1993 |
| JP | 2007-077028 | 3/2007 |
| JP | 2007-119378 | 5/2007 |
| JP | 2011-116753 | 6/2011 |
| WO | 2007/055598 | 5/2007 |
| WO | 2007/061022 | 5/2007 |
| WO | 2007/079581 | 7/2007 |
| WO | 2012/026495 | 3/2012 |

OTHER PUBLICATIONS

International Search Report dated Aug. 20, 2013 in International (PCT) Application No. PCT/JP2013/063689.
Shackelford et al., "The LKB1-AMPK pathway: metabolism and growth control in tumour suppression", Nature Reviews Cancer, vol. 9, No. 8, Aug. 2009, pp. 563-575.
Mihaylova et al., "The AMPK signalling pathway coordinates cell growth, autophagy and metabolism", Nature Cell Biology, vol. 13, No. 9, Sep. 2011, pp. 1016-1023.
Hardie et al., "AMPK: a nutrient and energy sensor that maintains energy homeostasis", Nature Reviews Molecular Cell Biology, vol. 13, No. 4, Apr. 2012, pp. 251-262.
Sanz et al., "The Mitochondrial Prohibitin Complex is Essential for Embryonic Viability and Germline Function in *Caenorhabditis elegans*", The Journal of Biological Chemistry, vol. 278, No. 34, Aug. 22, 2003, pp. 32091-32099.
Berger et al., "Prohibitin Family Members Interact Genetically with Mitochondrial Inheritance Components in *Saccharomyces cerevisiae*", Molecular and Cellular Biology, vol. 18, No. 7, Jul. 1998, pp. 4043-4052.
He et al., "A Repressive Role for Prohibitin in Estrogen Signaling", Molecular Endocrinology, vol. 22(2), Oct. 11, 2007, pp. 344-360.
Merkwirth et al., "Prohibitins control cell proliferation and apoptosis by regulating OPA1-dependent cristae morphogenesis in mitochondria", Genes & Development, vol. 22, Feb. 15, 2008, pp. 476-488.
Jupe et al., "Prohibitin in Breast Cancer Cell Lines: Loss of Antiproliferative Activity is Linked to 3' Untranslated Region Mutations", Cell Growth & Differentiation, vol. 7, No. 7, Jul. 1996, pp. 871-878.
Sievers et al., "Prohibitins are Required for Cancer Cell Proliferation and Adhesion", PLoS ONE, vol. 5, Issue 9, e12735, Sep. 14, 2010, pp. 1-9.
Sanz et al., "Prohibitin couples diapause signalling to mitochondrial metabolism during ageing in *C. elegans*", Nature, vol. 461, Issue 7265, Aug. 8, 2009, pp. 793-797.
Zubovych et al., "Mitochondrial Dysfunction Confers Resistance to Multiple Drugs in *Caenorhabditis elegans*", Molecular Biology of the Cell, vol. 21, No. 6, Mar. 15, 2010, pp. 956-969.
Choi et al., "Sanguinarine is an allosteric activator of AMP-activated protein kinase", Biochemical and Biophysical Research Communications, vol. 413, Aug. 23, 2011, pp. 259-263.
Garcia-Ruiz et al., "Mitochondrial Complex I Subunits are Decreased in Murine Nonalcoholic Fatty Liver Disease: Implication of Peroxynitrite", Journal of Proteome Research, vol. 9, No. 5, Nov. 3, 2010, pp. 2450-2459.
Cayón et al., "Gene expression in obese patients with non-alcoholic steatohepatitis", Rev Esp Enferm Dig (Madrid), vol. 100, No. 4, 2008, pp. 212-218.
Takahashi et al., "Mild caloric restriction up-regulates the expression of prohibitin: A proteome study", Biochemical and Biophysical Research Communications, vol. 405, No. 3, Jan. 20, 2011, pp. 462-467.
Supplemental Partial European Search Report dated Dec. 22, 2015 in corresponding European Patent Application No. 13790343.1.

AMPK ACTIVATOR SCREENING METHOD, AND AMPK ACTIVATOR

TECHNICAL FIELD

The present invention relates to an AMPK activator and a method for screening the same. The present invention also relates to a PHB-AMPK complex.

BACKGROUND ART

A 5'AMP-activated protein kinase (hereinafter also referred to as AMPK) is a phosphotransferase that is conserved in various living organisms and is involved in energy metabolism of cells, such as uptake of glucose into cells, oxidation of lipids, and generation of glucose transporter 4 (GLUT4) and mitochondria. AMPK is a complex consisting of three subunits of α, β and γ subunits, and is activated through phosphorylation of the 172th threonine of the a subunit by an upstream kinase. The activated AMPK is known to inhibit an anabolic pathway of the metabolism and to accelerate a catabolic pathway corresponding to an energy production pathway.

When AMPK is activated, synthesis of fatty acids, proteins and the like corresponding to the anabolic pathways is inhibited to inhibit cell growth while the energy production pathway of oxidation of fatty acids and glucose transport and like corresponding to the catabolic pathways are accelerated. Accordingly, the activation of AMPK is known to exhibit favorable effects in the prevention/treatment of adult diseases such as diabetes, diabetic complication, lipid metabolism abnormality, non-alcoholic steatohepatitis, arterial sclerosis, obesity and metabolic syndrome, and is recently presumed to exhibit favorable effects in the prevention/treatment of cancers, polycystic kidney, cardiac ischemia, dementia, neurodegenerative diseases, and circadian rhythm sleep disorder (Non Patent Literatures 1 to 3). The activation mechanism of AMPK has, however, not been identified yet.

On the other hand, a prohibitin (hereinafter also referred to as PHB) is a protein highly conserved in plants, fungi, single-cell eukaryotes, animals and the like, and a human PHB is disclosed in, for example, Patent Literature 1. PHB is known to form a cyclic structure constructed by two subunits, that is, prohibitin 1 (hereinafter also referred to as PHB1) and prohibitin 2 (hereinafter also referred to as PHB2). PHB1 and PHB2 together form a complex interdependently, and a deficiency of either PHB1 or PHB2 induces a deficiency of the whole complex formed by these proteins (Non Patent Literatures 4 to 7). While it is reported that PHB is present and functions in a mitochondrial inner membrane, it is also reported that PHB is involved in transcriptional control in a nucleus.

PHB was initially identified as a cell growth inhibition factor. It has been recently revealed, however, that the growth inhibition function is not a function of PHB but derived from a 3'UTR of a PHB gene, and furthermore, it has been revealed that PHB itself rather positively controls cell growth (Non Patent Literatures 8 and 9). Besides, Non Patent Literature 10 describes that a PHB complex is involved in control of lipid metabolism in a nematode to pertain to the lifetime, and Patent Literature 2 describes that PHB2 controls adipose differentiation. The molecular mechanism of PHB involved in these phenomena, however, has not yet been identified.

Besides, Patent Literature 3 discloses a bond between PHB and biguanide, that is, an oral hypoglycemic agent. Furthermore, it is disclosed that the actions of biguanide (namely, activation of AMPK and an ATP lowering action) are inhibited by knockdown of PHB in rat hepatic cells.

The relationship between PHB and AMPK has, however, not been identified yet.

CITATION LIST

Patent Literature

Patent Literature 1: Japanese Patent Application Laid-Open No. H05-271294
Patent Literature 2: Japanese Patent Application Laid-Open No. 2011-116753
Patent Literature 3: Japanese Patent Application Laid-Open No. 2007-77028

Non Patent Literature

Non Patent Literature 1: Nat. Rev. Cancer., 9(8): pp. 563-75 (2009)
Non Patent Literature 2: Nat Cell Biol., 13(9): pp. 1016-23 (2011)
Non Patent Literature 3: Nat Rev Mol Cell Biol., 13(4): pp. 251-62 (2012)
Non Patent Literature 4: J. Biol. Chem., vol. 278, p. 32091 (2003)
Non Patent Literature 5: Mol. Cell. Biol., vol. 18, p. 4043 (1998)
Non Patent Literature 6: Mol. Endocrinol., vol. 22, p. 344 (2008)
Non Patent Literature 7: Genes. Dev., vol. 22, p. 476 (2008)
Non Patent Literature 8: Cell Growth Differ., 7(7): p. 871-8 (1996)
Non Patent Literature 9: PLoS One. 5(9): e12735. (2010)
Non Patent Literature 10: Nature. 461(7265): pp. 793-7 (2009)

SUMMARY OF INVENTION

Technical Problem

The identification of the molecular mechanism of AMPK activation to find a molecule to accelerate AMPK activation leads to development of a therapeutic/preventive agent for adult diseases such as diabetes, lipid metabolism abnormality, obesity and metabolic syndrome, cancers and the like. Accordingly, one object of the present invention is to identify the molecular mechanism of the AMPK activation and its relation to PHB. Another object of the present invention is to provide an AMPK activator and a tool to be used for searching it on the basis of the identified molecular mechanism.

Solution to Problem

The present inventors have found, on the basis of results of experiments for analyzing expression of various genes in human cells in which siRNA against PHB1 or PHB2 is introduced, namely, human cells in which PHB is knocked down, that the knockdown of PHB does not inhibit but rather accelerates the phosphorylation of the 172th threonine of an AMPK α subunit (hereinafter also referred to as AMPKα). Specifically, it has been revealed that the knockdown of PHB accelerates the AMPK activation. Besides, the present inventors have also found that PHB is bound to AMPK to form a complex and that AMPK is activated by inhibiting this interaction. On the basis of these findings, the present inventors have accomplished the present invention.

Specifically, the present invention provides a method for screening an AMPK activator, wherein inhibition of an interaction between prohibitin and AMPK is used as an index. This screening method utilizes a molecular mechanism in which PHB and AMPK directly interact with each other to form a complex. This molecular mechanism was newly found by the present inventors, and hence, an AMPK activator based on a unique action mechanism can be obtained. The AMPK activator can be applied to the treatment/prevention of adult diseases such as diabetes, lipid metabolism abnormality, obesity, and metabolic syndrome, cancers and the like.

The above-described method preferably comprises the steps of measuring an interaction between PHB and AMPK in the presence of a test compound; and determining the test compound as an AMPK activator if an interaction between PHB and AMPK in the presence of the test compound is weaker than an interaction between PHB and AMPK in the absence of the test compound.

The above-described method preferably comprises the steps of: adding, to one of PHB and AMPK immobilized on a carrier, a solution comprising a test compound and the other of PHB and AMPK; measuring an interaction between PHB and AMPK after removing the solution; and determining the test compound as an AMPK activator if an interaction between PHB and AMPK in the presence of the test compound is weaker than an interaction between PHB and AMPK in the absence of the test compound.

Alternatively, the above-described method preferably comprises the steps of adding a solution comprising a test compound to one of PHB and AMPK immobilized on a carrier; adding a solution comprising the other of PHB and AMPK; measuring an interaction between PHB and AMPK after removing the solutions; and determining the test compound as an AMPK activator if an interaction between PHB and AMPK in the presence of the test compound is weaker than an interaction between PHB and AMPK in the absence of the test compound.

In the above-described method, a method for measuring the interaction between PHB and AMPK is preferably a method utilizing a proximity effect.

In the above-described method, PHB is preferably PHB1.

In the above-described method, AMPK is preferably an AMPK β subunit.

In the above-described method, PHB is preferably a fusion protein. Besides, AMPK is also preferably a fusion protein.

The present invention also provides a PHB-AMPK complex formed by mixing isolated PHB and isolated AMPK.

The present invention also provides a PHB-AMPK complex formed by allowing PHB overexpressed in cells and AMPK overexpressed in cells to bind each other.

The present invention also provides an AMPK activator comprising, as an active ingredient, a compound inhibiting an interaction between PHB and AMPK. In relation to the AMPK activator, PHB is preferably PHB1. In relation to the AMPK activator, AMPK is preferably an AMPK β subunit.

Advantageous Effects of Invention

According to the screening method of the present invention, an AMPK activator based on a unique action mechanism different from those of existing pharmaceutical agents can be obtained. Since such a compound is found, a drug effective for treating/preventing adult diseases such as diabetes, lipid metabolism abnormality, obesity and metabolic syndrome, cancers and the like can be developed.

DESCRIPTION OF EMBODIMENTS

The present invention will now be described in detail with reference to preferred embodiments.

The present invention provides a method for screening an AMPK activator, wherein inhibition of an interaction between prohibitin and AMPK is used as an index. The present invention also provides an AMPK activator inhibiting an interaction between PHB and AMPK.

Herein, unless otherwise mentioned, the term "PHB" refers to PHB1 and/or PHB2, and the term "AMPK" refers to one or more of AMPKα, AMPKβ and AMPKγ subunits. Besides, the term "AMPK activation" simply means activation of AMPK, representatively means phosphorylation of AMPK, and more representatively means phosphorylation of the 172th threonine of AMPKα.

According to the present invention, an AMPK activator having a mechanism that inhibits an interaction between PHB and AMPK can be screened to be provided.

An AMPK activator screening method according to a first embodiment comprises the steps of: measuring an interaction between PHB and AMPK in the presence of a test compound; and determining the test compound as an AMPK activator if an interaction between PHB and AMPK in the presence of the test compound is weaker than an interaction between PHB and AMPK in the absence of the test compound.

Biological species from which PHB and AMPK used in the present invention are derived are not especially limited, and examples include plants, fungi, single-cell eukaryotes and animals. PI-113 is derived from preferably an animal, more preferably a mammal such as a human, a rat, a mouse, a pig or a monkey, and further preferably a human.

Each of PHB and AMPK used in the present invention may be a full length protein or may be constituted by a partial peptide or protein. If PHB or AMPK is constituted by a partial peptide or protein, such a partial peptide or protein includes a site where the interaction of these proteins occurs. An example of a site of AMPK where the interaction with PHB occurs includes a C-terminal of AMPKβ, and in particular, 264th to 270th amino acid residues of human AMPKβ.

Besides, from the viewpoint that the protein can be easily isolated and purified, each of PHB and AMPK is preferably a fusion protein containing a full length protein or a partial peptide or protein. Examples of the fusion protein include a GST fusion protein, a His fusion protein, a FLAG fusion protein, an HA fusion protein and a Myc fusion protein.

Furthermore, each of PHB and AMPK may have mutation. A mutant does not affect the interaction between these proteins, and preferably, a site having the mutation is not a site involved in the interaction.

Each of PHB and AMPK may be a protein extracted from cells or obtained from in vitro translation. The protein extracted from cells may be an endogenous protein or a protein overexpressed in the cells. Alternatively, each of PHB and AMPK may be a protein commercially available from, for example, Abnova Corp.

If an endogenous protein is used, each of PHB and AMPK is extracted from, for example, hepatic cells; interstitial cells; Langerhans' cells; splenic cells; nerve cells such as glia cells; pancreatic β cells; bone marrow cells; epidermal cells; epithelial cells; endothelial cells; muscle cells such as smooth muscle cells; fibroblasts; fibrous cells; fat cells; immunocytes such as macrophages, T cells, B cells, natural killer cells, mast cells, neutrophic leukocytes, basocytes, acidocytes or monocytes; bone cells such as chondrocytes, osteoblasts or osteoclasts; or mammary cells. These cells may be normal cells or may be cancer cells, precursor cells or stem cells. Alternatively, the protein may be extracted from a tissue or an organ containing any of these cells.

Means for overexpressing the protein in cells can be appropriately selected by a person skilled in the art. The means preferably includes a step of introducing a vector for overexpressing the protein into cells and synthesizing the protein in the cells. The cells to be used are not especially limited, and examples include cells derived from a mammal such as a human, a mouse or a rat, and E. coli. Examples of the overexpression vector include a plasmid vector and a virus vector. Examples of a method for introducing an overexpression vector into cells include known gene introduction methods such as a calcium phosphate method, a lipofection method, a DEAE-dextran method, an electroporation method, a microinjection method, and a viral infection method. The protein to be overexpressed in cells is preferably a fusion protein having a tag such as GST, His, FLAG, HA or Myc. If the protein has such a tag, the protein can be more easily isolated. Besides, the tag may be added to either the N-terminal or the C-terminal of a fusion protein, and is added preferably to a site not affecting the interaction between PHB and AMPK. Cells, a vector and a promoter to be used for the overexpression, the type of tag, a method for introducing a vector and the like may be appropriately selected by a person skilled in the art.

A method for extracting a protein from cells is known to a person skilled in the art. A protein can be extracted, for example, from a cell lysate. In this method, cells are lysed in, for example, a buffer containing a surface active agent such as NP40 or Triton. The protein may be further isolated from the resultant cell lysate. Examples of a method for isolating a protein includes an isolation method utilizing an antigen-antibody reaction, immobilized metal ion affinity chromatography, and a method utilizing a carrier such as Sepharose.

Alternatively, PHB and AMPK may be obtained by using an in vitro translation system. The in vitro translation system is known to a person skilled in the art, and an example includes TNT T7 Quick Coupled Transcription/Translation System (Promega).

PHB and AMPK to be used may be the same as or different from each other in the length, the species, tissue or cell type of the origin, the presence of mutation, the obtaining method, and the like. For example, these proteins may be a combination of a full length PHB and a partial peptide of AMPK, or a combination of an endogenous PHB and AMPK obtained by the in vitro translation.

PHB may be PHB1 or PHB2, or a complex of these proteins. PHB is preferably PHB1. Besides, AMPK may be any of AMPKα, AMPKβ and AMPKγ subunits, or may be a complex of these subunits. Particularly, AMPK is preferably AMPKβ.

The test compound is not especially limited, and may be a synthetic compound or a compound present in a natural product extract. Examples of the test compound include a synthetic compound, a natural compound, a plant extract, an animal extract, a fermentation product, a commercially available reagent, and a compound selected from a compound library. The molecular species of the test compound is also not especially limited, and examples include a low molecular weight compound, a peptide, a protein, a sugar and a nucleic acid.

Herein, the "interaction" may be direct binding to form a complex, or may be indirect interaction through another molecule to form a complex. However, in order to further improve the sensitivity and specificity of detection and further decrease false positive in a screening result, the direct binding to form a complex is preferred.

To use an interaction between PHB and AMPK as an index means that the degree of influence of the test compound on an interaction between PHB and AMPK is used as an identification standard. For example, if an interaction between PHB and AMPK in the presence of the test compound is weaker than an interaction therebetween in the absence of the test compound, the test compound can be identified as an AMPK activator.

A decrease rate of the interaction between PHB and AMPK in the presence of an AMPK activator varies depending on an evaluation method. For example, the interaction between PHB and AMPK in the presence of an AMPK activator (of 10 μM) is preferably 50% or less, more preferably 10% or less, and further preferably 5% or less of that in the absence of the AMPK activator.

As a method for measuring the interaction between PHB and AMPK, a system for measuring a protein-protein interaction known to a person skilled in the art can be used. Now, systems for measuring a protein-protein interaction of the present embodiment will be described in detail, but the measurement method is not limited to the following measurement systems.

The method for measuring a protein-protein interaction preferably includes a step of quantitatively determining the interaction. Examples of known methods for quantitatively determining an interaction include a method for directly measuring the interaction as a numerical value, such as a method utilizing an enzyme reaction, a method of measuring a fluorescence intensity, a method of measuring transcription or activation of a reporter gene or a method utilizing a radioactive substance, and a method in which a measurement result of the interaction is once captured as an image to measure dots or the like of the image. Alternatively, a labeled antibody to one of the proteins may be used for measuring the interaction. From the viewpoint of attaining objectivity of a measurement result and achieving high throughput screening, the interaction is preferably directly measured as a numerical value.

In the above-described measurement method, in order to easily measure the interaction between PHB and AMPK, at least one of the proteins is labeled. The label of the protein is not especially limited, and examples include an enzyme label using HRP, HA or the like, a fluorescent label using Cy3, Cy5, FAM or the like, a label using a coloring substance such as diaminobenzidine (DAB), 3,3',5,5-etramethylbenzidine (TMB), 3-amino-9-ethylcarbazole (AEC) or the like, and a radioactive label. Such a label is preferably added to a site exposed on the surface of the protein if the interaction between PHB and AMPK is not affected and if the protein has a higher-order structure.

The interaction between MB and AMPK can be measured also by a co-immunoprecipitation assay. The co-immunoprecipitation assay is a method in which a complex containing a target protein is precipitated by using an antibody to the target protein and the presence or absence of another protein in the precipitated complex is detected by imunoblotting so as to determine the interaction between the proteins.

If the co-immunoprecipitation assay is used as the method for measuring the protein-protein interaction, as typical procedures, cultured cells are first lysed, a carrier or a non-specific antibody is added to the resulting cell lysate, and the resultant is centrifuged to remove non-specific binding. Next, a carrier and an antibody to either PHB or AMPK are added to be bound, and the resultant is centrifuged to precipitate complexes. Examples of the carrier include Sepharose beads, agarose beads, Protein G beads and Protein A beads. The precipitated complexes are separated in accordance with size by SDS-PAGE and then transferred to a membrane such as PVDF, and an antibody to the other protein is added thereto as a primary antibody. Next, a labeled secondary antibody recognizing the primary antibody is added thereto to measure the amount of secondary antibody bound to the primary antibody. A labeling method is not especially limited, and labels similar to those described above with respect to the proteins can be used.

Alternatively, the interaction between PHB and AMPK can be also measured by a GST pull down assay. In the GST pull down assay, one protein to be subjected to the interaction measurement is bound as a GST fusion protein to a Glutathione Sepharose carrier to form a carrier-protein complex. The presence or absence of the other protein in the thus obtained complex is detected by immunoblotting, and thus, the interaction between the proteins can be determined.

If the GST pull down assay is used as the method for measuring the protein-protein interaction of the present invention, a Glutathione Sepharose carrier is first bound to a GST fusion PHB protein or a GST fusion AMPK protein (hereinafter also referred to as GST-AMPK) to form a complex. A liquid containing the other protein is added to the resultant complex to be bound, and after sufficiently washing off an excessive liquid, the complex is separated by SDS-PAGE and is transferred to a membrane such as PVDF. It is detected by using a labeled antibody whether or not the added protein is bound to the carrier-protein complex, so as to determine the interaction between these proteins. The labeling method is not especially limited, and labels similar to those described above with respect to the proteins can be used.

Another method for measuring the protein-protein interaction can be appropriately selected by a person skilled in the art, and examples of the method include a Far Western assay, a protein fragment complementation assay (PCA), fluorescence resonance energy transfer (FRET), an alpha screen assay, time-resolved fluorescence resonance energy transfer (TR-FRET), and a method utilizing a proximity effect such as a scintillation proximity assay (SPA). Similarly, examples of a method for measuring a protein-protein interaction in cells include bioluminescence resonance energy transfer (BRET), fluorescence correlation spectroscopy (FCCS), bimolecular fluorescent complementation (BiFC), and Duolink in situ Proximity ligation assay (PLA) (Olink Bioscience).

Besides, a two-hybrid assay utilizing a reporter gene, surface plasmon resonance (SPR) such as the Biacore system, or the like can be used as the method for measuring a protein-protein interaction.

On the basis of the interaction measured by any of the aforementioned methods, it is determined whether or not the test compound is an AMPK activator. Specifically, if an interaction between PHB and AMPK in the presence of the test compound is weaker than an interaction between PHB and AMPK in the absence of the test compound, the test compound is determined as an AMPK activator. The interaction between PHB and AMPK in the absence of the test compound may be measured at the same time as or separately from the measurement of the interaction between PHB and AMPK in the presence of the test compound.

An AMPK activator screening method according to a second embodiment of the present invention can comprise the steps of: adding, to one of PHB and AMPK immobilized on a carrier, a solution comprising a test compound and a solution containing the other of PHB and AMPK; measuring an interaction between PHB and AMPK after removing the solutions; and determining the test compound as an AMPK activator if an interaction between PHB and AMPK in the presence of the test compound is weaker than an interaction between PHB and AMPK in the absence of the test compound.

An AMPK activator screening method according to a third embodiment of the present invention can comprise the steps of: adding a solution comprising a test compound to one of PHB and AMPK immobilized on a carrier; adding a solution comprising the other of PHB and AMPK; measuring an interaction between PHB and AMPK after removing the solutions; and determining the test compound as an AMPK activator if an interaction between PHB and AMPK in the presence of the test compound is weaker than an interaction between PHB and AMPK in the absence of the test compound.

In the second and third embodiments, the carrier is not especially limited, and may be Sepharose beads, agarose beads, Protein G beads, Protein A beads or the like, or an anti-PHB or anti-AMPK antibody may be used. Besides, if a GST fusion protein, a His fusion protein, an HA fusion protein or the like is used, the protein may be immobilized by using corresponding beads or antibody. Furthermore, in order to improve the screening efficiency, the beads, the fusion protein or the antibody is more preferably immobilized on a multi-well plate. The multi-well plate has preferably 6 or more wells, more preferably 48 or more wells, preferably 96 or more wells, and extremely preferably 384 or more wells.

A protein to be immobilized may be PHB or AMPK.

The interaction between PHB and AMPK can be measured by reacting PHB with AMPK to bind them to each other. This reaction is preferably caused by adding, in the presence of the test compound, to one of PHB and AMPK immobilized on the carrier, a solution containing the other of PHB and AMPK, and allowing the resultant solution to stand still for 1 or more minutes at 0 to 100° C. Thereafter, a washing process for removing the solution and removing an excessive amount of protein not bound is preferably performed.

A method for measuring the interaction between PHB and AMPK is not especially limited, and any of the methods described above in the first embodiment can be used. From the viewpoint of achieving high throughput screening, however, a method in which a plurality of samples can be simultaneously measured is preferably employed. An example of such a method includes a method in which the protein to be added is labeled. Alternatively, after the step of adding the solution containing the other of PHB and AMPK, and/or after the washing process following this step, a labeled antibody to the added protein may be added for the measurement. Besides, a measurement method in which a measured value is changed in accordance with binding of the proteins, such as the FRET or the SPR, may be also employed.

On the basis of the interaction measured by any of the above-described measurement methods, it is determined whether or not the test compound is an AMPK activator. The determination step is the same as that described in the first embodiment.

The present invention can also provide an AMPK activator comprising, as an active ingredient, a compound inhibiting an interaction between PHB and AMPK. The AMPK activator is not especially limited, and is preferably determined as an AMPK activator among test compounds by performing the screening method of the present invention.

The AMPK activator is not especially limited, and may be a synthetic compound or a compound present in a natural product extract. Examples of the AMPK activator include a synthetic compound, a natural compound, a plant extract, an animal extract, a fermentation product, a commercially available reagent, and a compound selected from a compound library. The molecular species of the AMPK activator is also not especially limited, and examples can include a low molecular weight compound, a peptide, a protein, a sugar and a nucleic acid.

Besides, an example of the AMPK activator of the present invention can include a compound represented by the following formula (1) (5(2,4-dioxo-3-butylimidazolidin-1-yl) methyl-2-methoxy-N-[4-(4-fluorophenoxy)phenylmethyl] benzamide, hereinafter referred to also as the compound A) (International Publication No. 2012/26495).

The present invention can also provide a complex of PHB and AMPK (hereinafter also referred to as PHB-AMPK complex). This complex is formed by allowing isolated PHB and isolated AMPK to bind each other, or PHB overexpressed in cells and AMPK overexpressed in cells to bind each other. As methods for isolating these proteins and for overexpressing these proteins in cells, those described in the first embodiment can be used.

The complex can be used for further elucidating the interaction mechanism between PHB and AMPK. For example, by forming a PHB-AMPK complex to analyze the crystal structure, a binding site between PHB and AMPK can be identified. Such elucidation of the interaction mechanism between PHB and AMPK is useful for, for example, designing a drug targeting the complex. Methods for the crystal structure analysis are known, and an example includes X-ray structure analysis.

A drug or the like targeting the complex preferably has an effect of controlling the interaction between PHB and AMPK in the complex, and further preferably has an effect of negatively controlling the interaction between PHB and AMPK.

The origins of PHB and AMPK are not limited. Besides, PHB and AMPK may be fusion proteins. Examples of such a fusion protein include those described in the first embodiment.

Each of PHB and AMPK may be a full length protein, or a partial peptide or protein. Besides, each of PHB and AMPK may have mutation. If a complex formed from PHB and AMPK each having a variety of sites or a complex formed from PHB and AMPK each having no mutation, and one or more complexes formed from PHB and AMPK having mutations are used, interactions between PHB and AMPK in various complexes can be measured for comparison. Thus, sites that affect or do not affect the interaction, such as a binding site between PHB and AMPK, can be specified.

EXAMPLES

Now, the present invention will be more specifically described with reference to Examples, but it is noted that the present invention is not limited to these Examples.

Example 1: Knockdown of PHB Using siRNA

Human hepatoma cell line HepG2 cells were transfected with siRNA (Stealth RNAi, Invitrogen) against human PHB1 or human PHB2 using Lipofectamine RNAiMAX (Invitrogen).

Seventy-two hours after the transfection, RNA was extracted from siRNA transfected cells using RNeasy Mini Kit (Qiagen). The thus obtained RNA was reverse transcribed into a cDNA using High Capacity cDNA Reverse Transcription Kit (Applied Biosystems). The resultant cDNA was subjected to real-time PCR by TaqMan Gene (1)

Expression Assays (Applied Biosystems, PHB1: Hs_00855044_g1, PHB2: Hs_00200720_ml) using 7500 Fast Real-Time PCR system (Applied Biosystems), and thus, the influence of the knockdown of PHB1 or PHB2 on the amount of gene expression was detected.

The sequences of the respective siRNAs are as follows:

```
siPHB1:
                                    (SEQ ID NO: 1)
5'-UUGGCAAUCAGCUCAGCUGCCUUGG-3'

(SEQ ID NO: 2)
5'-CCAAGGCAGCUGAGCUGAUUGCCAA-3' siPHB2:
                                    (SEQ ID NO: 3)
5'-UACGAUUCUGUGAUGUGGCGAUCGU-3'

(SEQ ID NO: 4)
5'-ACGAUCGCCACAUCACAGAAUCGUA-3'
```

Figure 1:
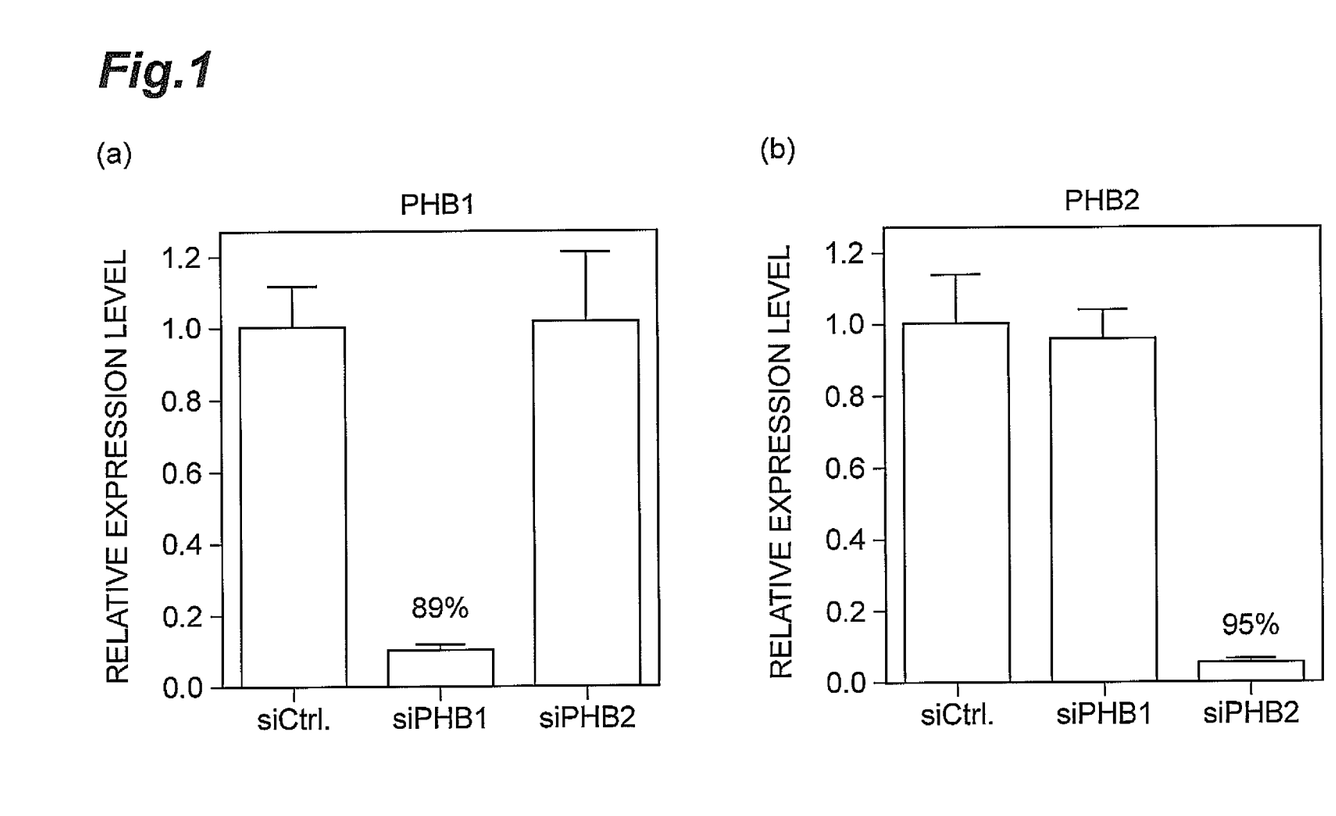
FIG. 1 shows the results of real-time PCR analysis of the RNAs obtained from HepG2 cells in which PHB is knocked down. The percentages correspond to the inhibition rates based on siCtrl.

The results of real-time PCR of PHB1 and PHB2 obtained with siRNA against PHB1 or PHB2 introduced are shown in FIG. 1. The introduction of siPHB1 and siPHB2 specifically depressed the amounts of transcription of PHB1 and PHB2, respectively. Accordingly, it was suggested that siPHB1 and siPHB2 efficiently and specifically inhibited the expression of the target genes.

Example 2: Influence of Knockdown of PHB on AMPK Phosphorylation

Human hepatoma cell line HepG2 cells were transfected with siRNA (Stealth RNAi, Invitrogen) against human PHB1 or human PHB2 using Lipofectamine RNAiMAX (Invitrogen). Seventy-two hours after the transfection, the resultant cells were lysed in a lysis buffer (1% NP-40, 25 mM Tris-HCl pH 7.4, 10 mM EDTA, 10 mM EGTA, 100 mM sodium fluoride, 10 mM sodium pyrophosphate, 10 mM sodium orthovanadate, and 10 mM β-glycerophosphoric acid, pH 7.4) to obtain a cell extract. The thus obtained cell extract was subjected to SDS-PAGE for separating proteins contained in the cell extract in accordance with their sizes. Thereafter, the separated proteins were transferred to a PVDF membrane, and subjected to Western blotting using anti-phosphorylated AMPKα antibody (Cell Signaling Technology) and anti-AMPKα antibody (Cell Signaling Technology), anti-PHB1 antibody (SantaCruz Biotechnology) and anti-PHB2 antibody (Millipore).

Figure 2:
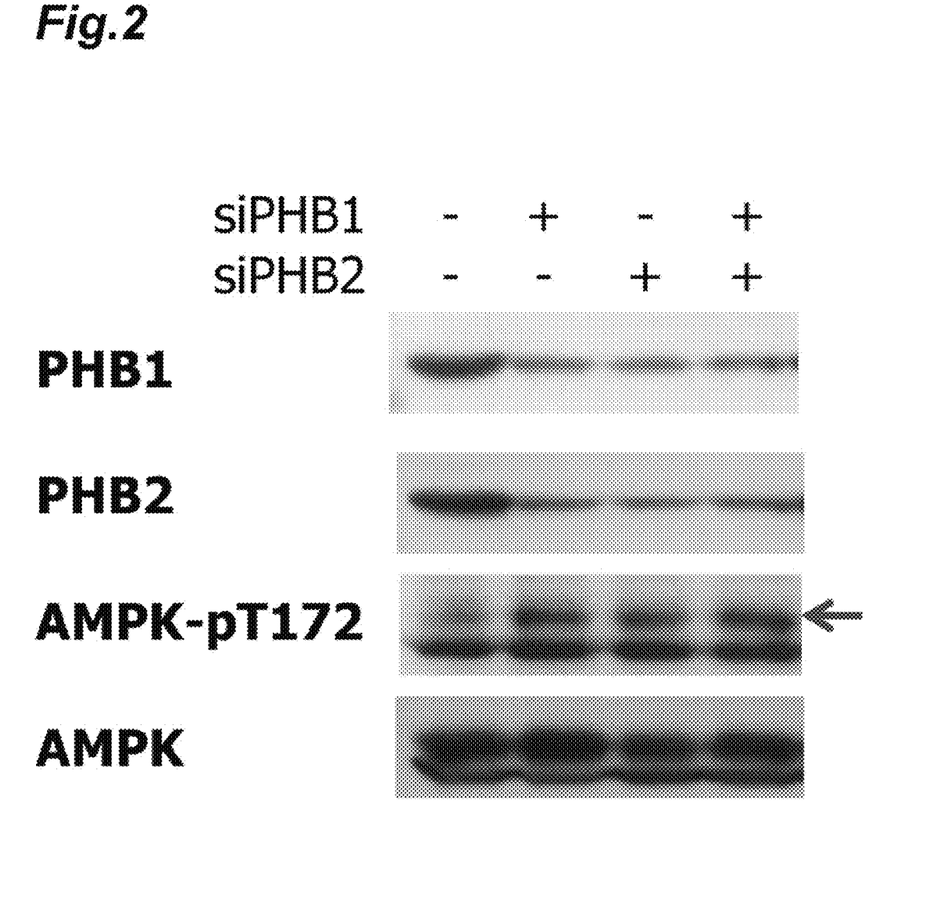
FIG. 2 shows the results of Western blotting analysis of the protein obtained from HepG2 cells in which PHB is knocked down. The arrow shows the band position of a phosphorylated AMPK. AMPK-pT172 corresponds to AMPKα, in which the 172th threonine is phosphorylated.

The results of Western blotting of the phosphorylation of AMPKα with PHB1 or PHB2 knocked down are shown in FIG. 2. No matter which of siRNAs against PHB1 and PHB2 was used, the amount of PHB1 and PHB2 decreased and the amount of phosphorylated AMPKα increased. At this point, the amount of AMPKα did not change. Accordingly, it was suggested that the activation of AMPK is induced by knocking down of PHB1 or PHB2.

Example 3: Confirmation of Interaction Between PHB and AMPK

Co-immunoprecipitation was performed in order to examine a possibility that PHB is involved in the control of AMPK through the interaction. Anti-IgG antibody was used as a negative control.

Protein G Sepharose (GE Healthcare) was added to a cell extract prepared from HepG2 cells, and the resultant was centrifuged to remove non-specific binding. Anti-PHB1 antibody (SantaCruz Biotechnology) or anti-AMPKα antibody (Cell Signaling Technology) and Protein G Sepharose were added to the supernatant, and the resultant was incubated for 4 hours at 4° C. for binding, followed by centrifugation for removing an excessive amount of cell extract. After removing non-specific binding by washing, a complex bound to Protein G Sepharose was purified as a co-immunoprecipitate. The thus obtained co-immunoprecipitate was separated by SDS-PAGE in accordance with size, the resultant was transferred to a PVDF membrane, and Western blotting was performed using anti-PHB1 antibody and anti-AMPKα antibody for the co-immunoprecipitate obtained using anti-PHB1 antibody, and using anti-AMPKα antibody, anti-AMPKβ antibody (Cell Signaling Technology), anti-PHB1 antibody and anti-PHB2 antibody for the co-immunoprecipitate obtained using anti-AMPKα antibody, so as to detect whether or not PHB1 and AMPKα protein were coprecipitated.

Figure 3:
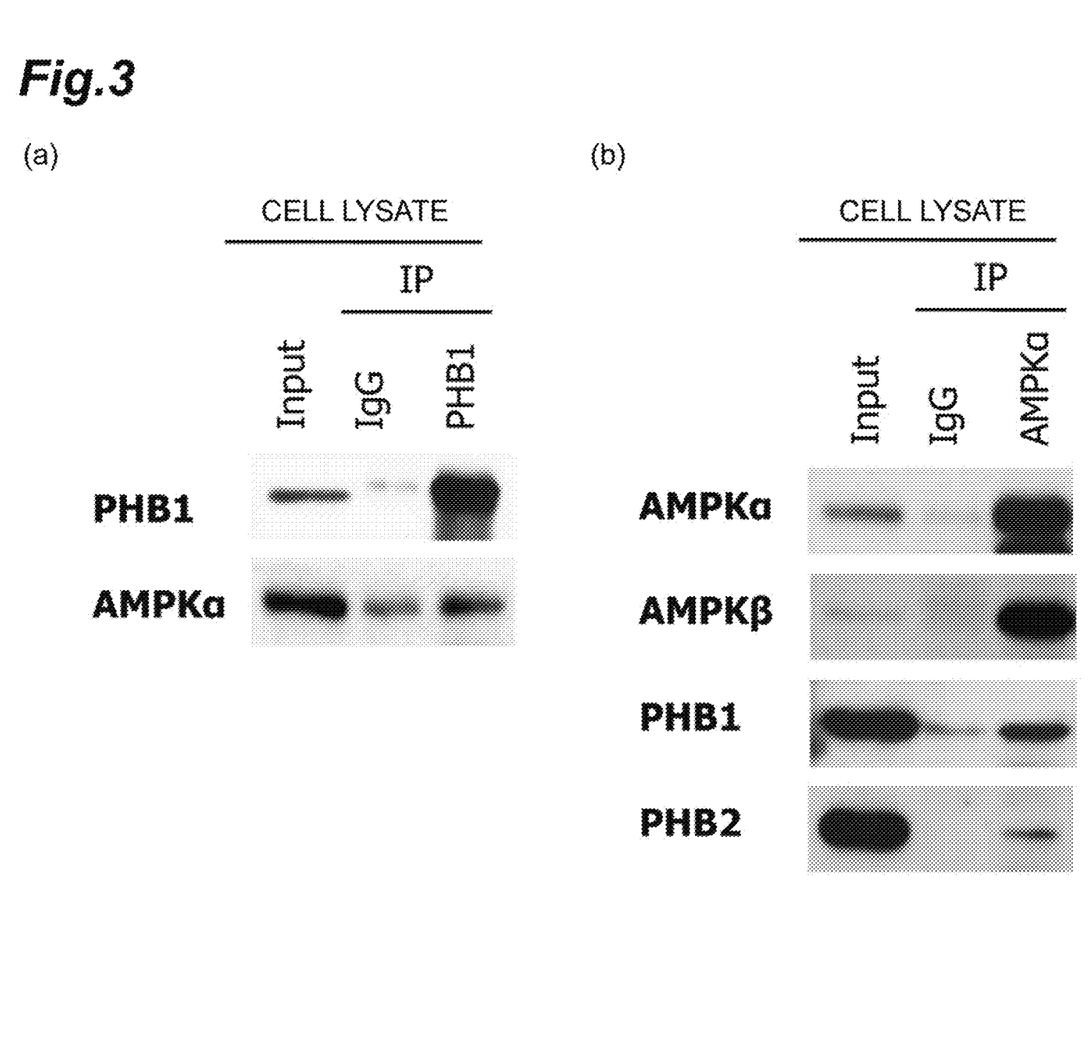
FIG. 3 shows the results of co-immunoprecipitation and immunoblot of HepG2 cells. IP corresponds to an antibody used in the co-immunoprecipitation.

The results of co-immunoprecipitation performed by using anti-PHB1 antibody are shown in FIG. 3(*a*). In the co-immunoprecipitate, AMPKα precipitated with PHB1 was detected.

The results of co-immunoprecipitation performed using anti-AMPKα antibody are shown in FIG. 3(*b*). In the co-immunoprecipitate, AMPKβ, PHB1 and PHB2 precipitated with AMPKα were detected.

AMPKα was detected in the co-immunoprecipitate obtained using anti-PHB1 antibody. In addition, PHB1 and PHB2 were detected in the co-immunoprecipitate obtained using anti-AMPKα antibody on the contrary. These results suggest that PHB and AMPK interact with each other in cells to form a complex.

Example 4: Confirmation of Direct Interaction Between PHB and AMPK

A possibility of a direct interaction between PHB and AMPK was examined by using GST pull down assay.

Specifically, Glutathione Sepharose 4 Fast Flow carrier (GE Healthcare) was bound to each of commercially available GST protein, a GST fusion PHB1 protein (hereinafter also referred to as GST-PHB1 protein) (Abnova Corp.) and a GST fusion PHB2 protein (hereinafter also referred to as the GST-PHB2 protein) (Abnova Corp.) to obtain GST carrier-protein complexes. Each of the GST carrier-protein complexes and AMPK (Calbiochem) were incubated in a NET buffer (0.5% NP-40, 50 mM Tris-HCl pH 7.5, 50 mM sodium chloride, and 5 mM EDTA) for 3 hours at 4° C. for binding. After washing the resultant with a NET buffer, a sample buffer (50 mM Tris-HCl pH 6.8, 2% SDS, 10% glycerin, 1% β-mercaptoethanol, 12.5 mM EDTA, and 0.02% bromophenol blue) was added thereto to prepare a sample. The thus obtained sample was separated by SDS-PAGE, the resultant was transferred to a PVDF membrane and subjected to Western blotting using anti-AMPKα and anti-GST antibodies, so as to detect whether or not AMPK was bound to GST protein, GST-PHB1 protein or GST-PHB2 protein bound to Gluthathione Sepharose to be pulled down.

Figure 4:
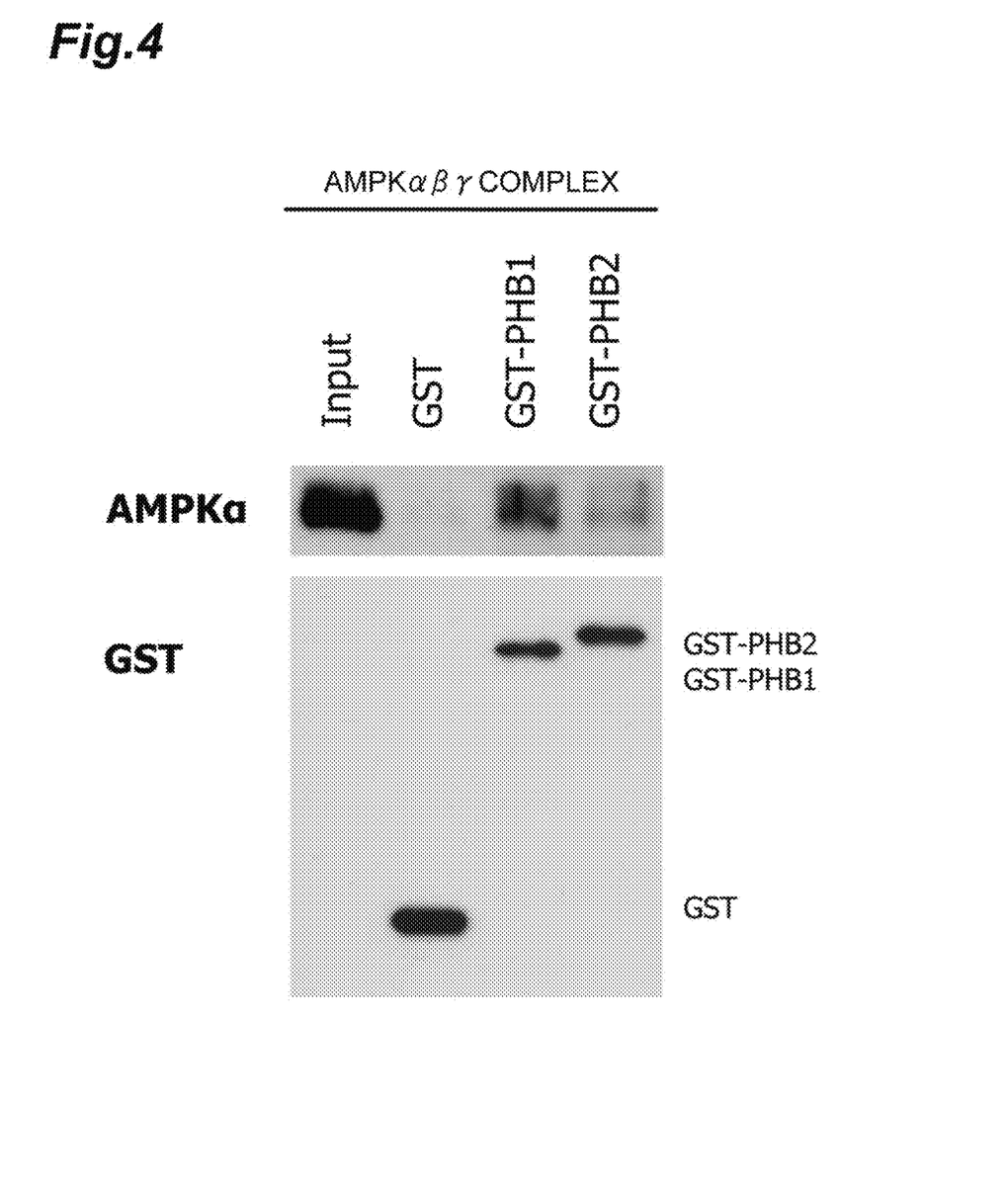
FIG. 4 shows the results of interaction, obtained by a GST pull down assay, between PHB1 or PHB2 and an AMPK αβγ complex.

The results of GST pull down assay are shown in FIG. 4. In a complex pulled down by GST protein, AMPKα was not detected, but in complexes pulled down by GST-PHB1 protein and GST-PHB2 protein, AMPKα was detected. Besides, the amount of AMPKα detected in the complex pulled down by GST-PHB2 protein was smaller than the amount thereof detected in the complex pulled down by GST-PHB1 protein. Accordingly, it was revealed that PHB, particularly, PHB1 directly interacts with AMPK.

Example 5: Confirmation of Interaction Between PHB and AMPK Subunit

GST pull down assay was employed for identifying AMPK subunit interacting with PHB.

A GST carrier-protein complex was prepared in the same manner as in Example 4. [$^{35}$S] methionine (Perkin Elmer Corp.) labeled AMPKα, AMPKβ, AMPKγ, and PHB1 were prepared using TNT Quick Coupled Transcription/Translation systems (Promega), respectively. The GST carrier-protein complex was mixed with $^{35}$S labeled proteins, and GST pull down assay was performed in the same manner as in Example 4. The resultant sample was separated by SDS-PAGE, and it was detected, by autoradiography, whether or not $^{35}$S labeled proteins were pulled down by the GST carrier-protein complex.

Figure 5:
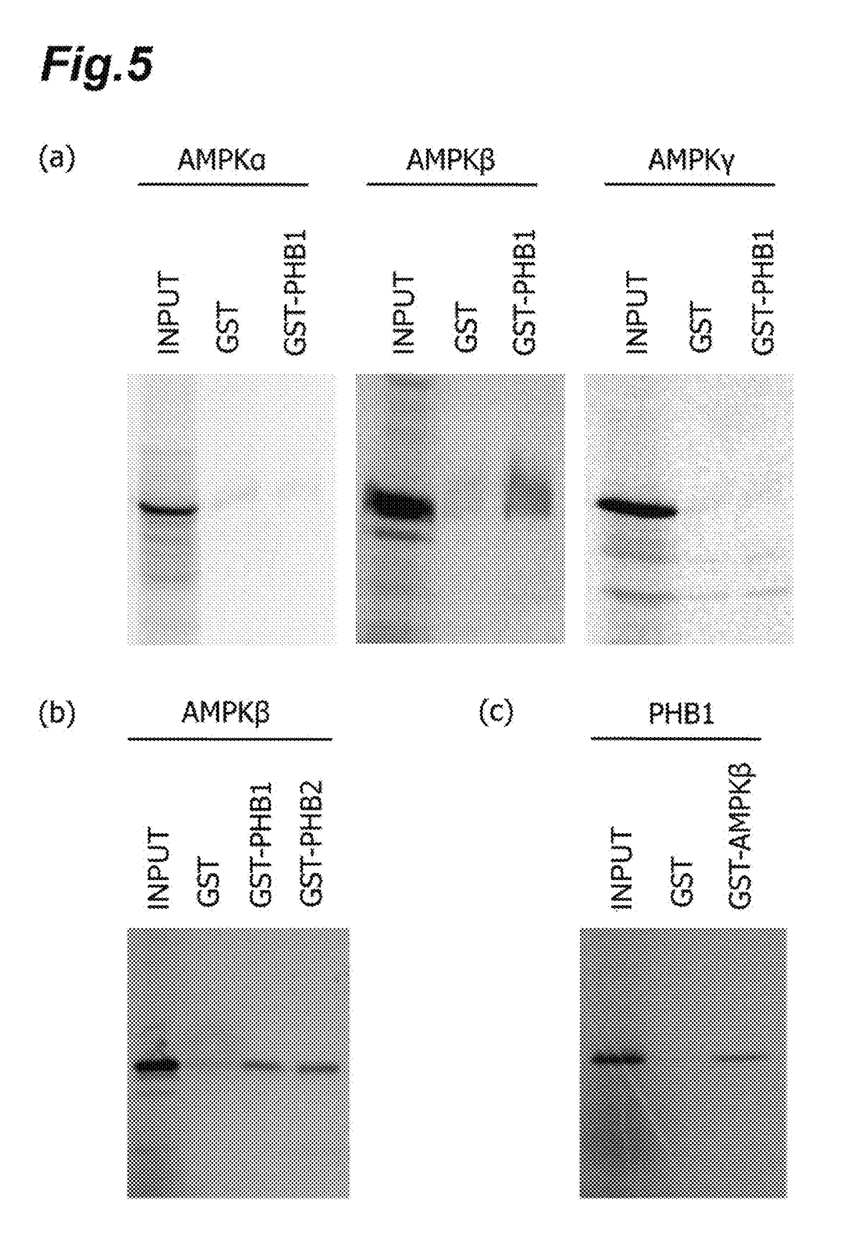
FIG. 5 shows the interaction, obtained by the GST pull down assay, between PHB1 or PHB2 and an AMPK α, β or γ subunit.

The results of the pull down assay are shown in FIG. 5. In a complex pulled down by GST protein, none of $^{35}$S labeled proteins was detected. In a complex pulled down by GST-PHB1 protein, $^{35}$S labeled AMPKα and $^{35}$S labeled AMPKγ were not detected but $^{35}$S labeled AMPKβ was detected (FIG. 5(a)). Besides, also in a complex pulled down by GST-PHB2 protein, $^{35}$S labeled AMPKβ was detected (FIG. 5(b)). On the contrary, also in a complex pulled down by GST-AMPKβ, $^{35}$S labeled PHB1 was detected (FIG. 5(c)). Accordingly, it was suggested that PHB1 and PHB2 interact through the AMPKβ subunit in AMPK complex.

Example 6: Identification of Region in AMPK β Subunit Important for Interaction with PHB In order to identify a region of the AMPK subunit important for the interaction with PHB, the following experiment was performed using a deletion mutant of the AMPK β subunit.

An expression vector for each of AMPK β subunits of full length or various deletion mutants having an HA tag (YPYDVPDYA; SEQ ID NO. 5) added to the N-terminal thereof, and an expression vector for PHB1 having a Flag tag (DYKDDDDK; SEQ ID NO. 6) added to its C-terminal were introduced into HepG2 cells using Lipofectamine LTX (Invitrogen), and the resultant cells were cultured overnight at 37° C. Immunoprecipitation was performed using anti-HA affinity matrix (Roche) in the same manner as in Example 3. Western blotting was performed using anti-HA antibody and anti-Flag antibody (both Cell Signaling Technology) to examine whether or not the AMPK subunit and PHB1 were coprecipitated.

Figure 6:
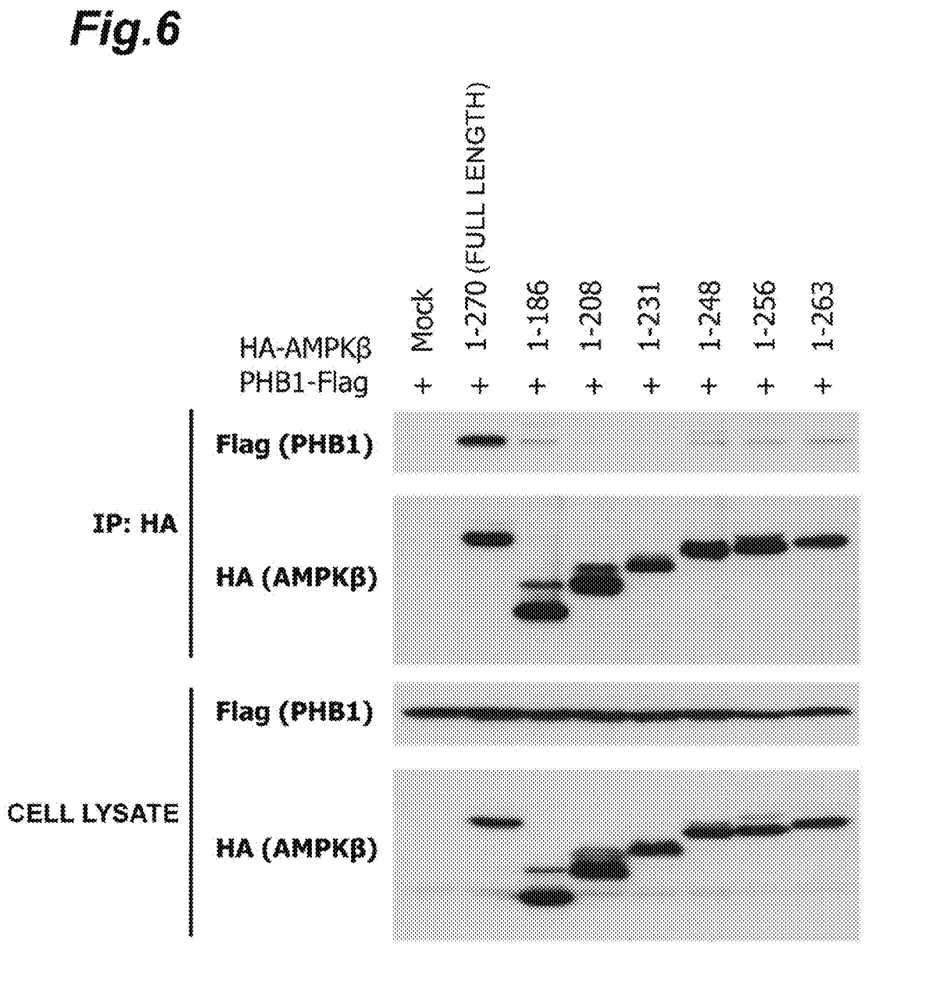
FIG. 6 shows the interaction, obtained by a co-immunoprecipitation assay, between PHB1 and an AMPK β subunit of full length or of a C-terminal deletion mutant.

The results are shown in FIG. 6. Since PHB1 was coprecipitated with the full length AMPK β subunit, it was confirmed that the AMPK β subunit interacts with PHB1 in cells. However, since PHB1 was not coprecipitated with the various C-terminal deletion mutants of the AMPK β subunit, it was revealed that the C-terminal (the 264th to 270th amino acid residues, in particular) of the AMPK β subunit is necessary for the interaction between the AMPK β subunit and PHB1.

Example 7: Influence of Compound a on Interaction Between PHB1 and AMPK

GST-PHB1 protein (500 ng) was bound to Glutathione Sepharose 4 Fast Flow (10 µL) to obtain a GST carrier-protein complex. Compound A (having a final concentration of 10 µM) and AMPK (100 ng) were added to the GST carrier-protein complex, and the resultant was incubated in a NET buffer (300 µL) for 3 hours at 4° C. After washing the resulting GST carrier-protein complex with a NET buffer, a sample buffer (50 µL) was added thereto to prepare a sample. The thus obtained sample was separated by SDS-PAGE and then transferred to a PVDF membrane, and Western blotting was performed to detect whether or not AMPK was bound to GST protein or GST-PHB1 protein bound to Glutathione Sepharose to be pulled down.

Figure 7:
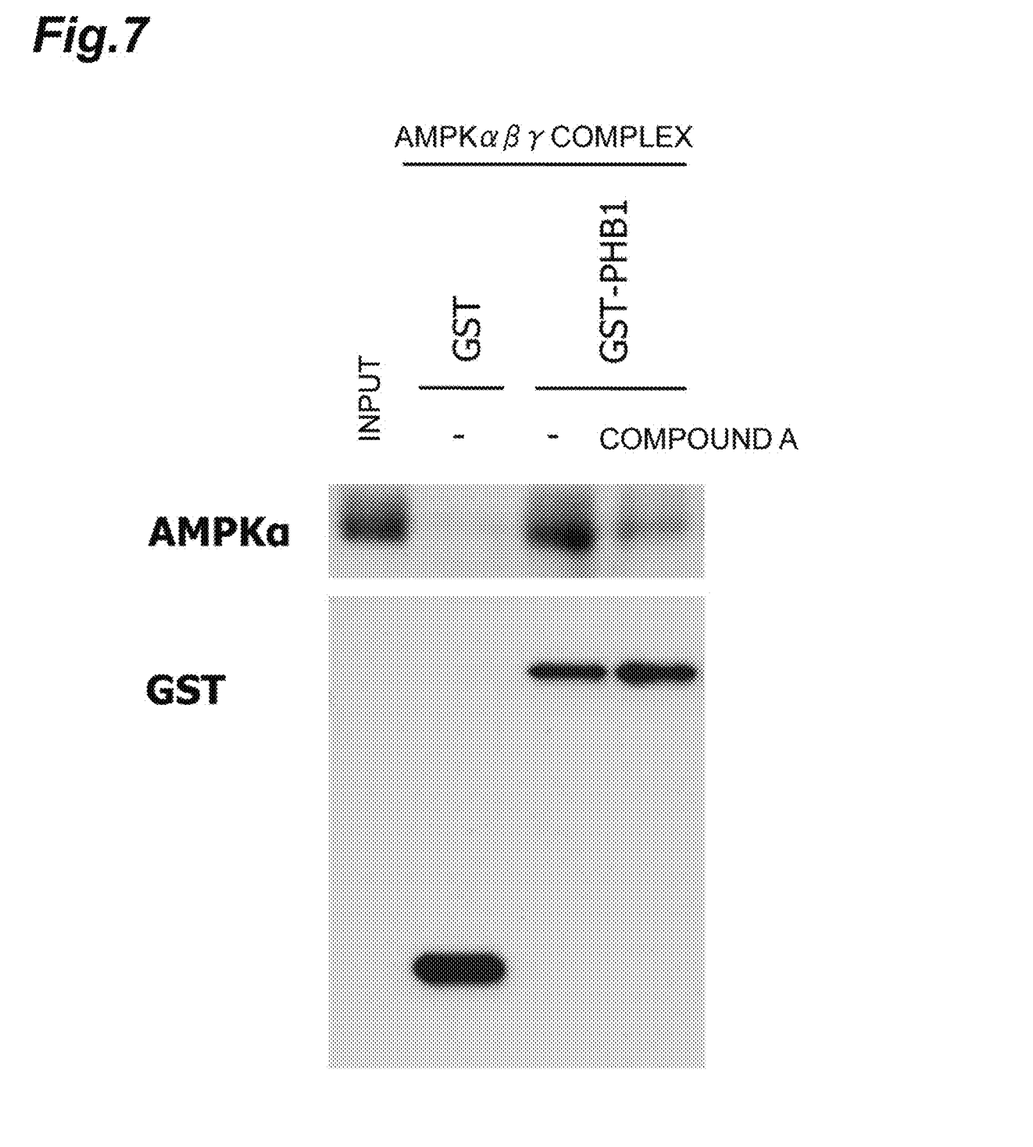
FIG. 7 shows the results obtained by pulling down and immunoblotting of GST fusion PHB1 protein in the presence of compound A.

In FIG. 7, AMPKα pulled down by GST-PHB1 protein was remarkably decreased by adding compound A. Accordingly, it was suggested that compound A inhibits the interaction between PHB1 and AMPK.

Example 8: Influence of Compound a on AMPKα Phosphorylation

Compound A was added to a HepG2 cell culture system to various final concentrations, and after culturing the resultant for 3 hours, the cells were lysed in a lysis buffer to obtain a cell extract. The thus obtained cell extract was used for performing SDS-PAGE so as to separate proteins contained in the extract in accordance with their sizes, and the resultant was transferred to a PVDF membrane to detect PHB1, PHB2, AMPKα and phosphorylated AMPKα by Western blotting.

Figure 8:
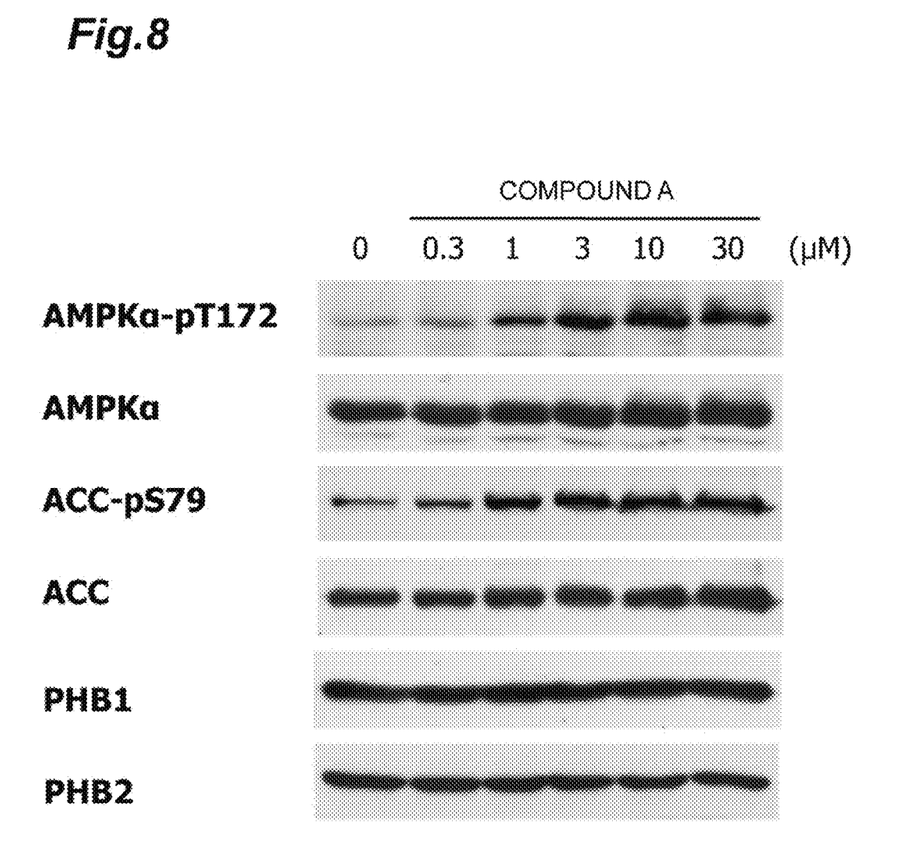
FIG. 8 shows the results of Western blotting analysis of the proteins obtained from HepG2 cells cultured in the presence of compound A at various concentrations. ACC corresponds to acetyl-CoA carboxylase, and ACC-pS79 corresponds to ACC in which the 79th serine is phosphorylated.

In FIG. 8, the results of Western blotting analysis of the phosphorylated AMPKα, AMPKα, ACC corresponding to the phosphorylation substrate of the phosphorylated AMPKα, phosphorylated ACC, PHB1, and PHB2 are shown on the concentration—dependence of compound A. It was found that levels of the phosphorylated AMPKα and the phosphorylated ACC were increased by compound A in a concentration-dependent manner. On the other hand, the addition of compound A does not remarkably affect the amounts of AMPKα, ACC, PHB1 and PHB2. Thus, it was revealed that compound A inhibits the interaction between PHB and AMPK to activate AMPK.

INDUSTRIAL APPLICABILITY

The screening method of the present invention provides an AMPK activator having an action mechanism completely different from those of conventional activators. Such a compound can be a drug effective for treating/preventing adult diseases such as diabetes, lipid metabolism abnormality, obesity and metabolic syndrome, cancers and the like.

The invention claimed is:

1. A method for screening for an AMPK activator, comprising using an inhibition of an interaction between a prohibitin and an AMPK as an index.

2. The method according to claim 1, comprising the steps of:

measuring an interaction between the prohibitin and the AMPK in the presence of a test compound; and determining the test compound as the AMPK activator if an interaction between the prohibitin and the AMPK in the presence of the test compound is weaker than an interaction between the prohibitin and the AMPK in the absence of the test compound.

3. The method according to claim 1, comprising the steps of:
   adding, to one of the prohibitin and the AMPK immobilized on a carrier, a solution comprising a test compound and the other of the prohibitin and the AMPK;
   measuring an interaction between the prohibitin and the AMPK after removing the solution; and
   determining the test compound as the AMPK activator if an interaction between the prohibitin and the AMPK in the presence of the test compound is weaker than an interaction between the prohibitin and the AMPK in the absence of the test compound.

4. The method according to claim 1, comprising the steps of:
   adding a solution comprising a test compound to one of the prohibitin and the AMPK immobilized on a carrier;
   adding a solution comprising the other of the prohibitin and the AMPK;
   measuring an interaction between the prohibitin and the AMPK after removing the solutions; and
   determining the test compound as the AMPK activator if an interaction between the prohibitin and the AMPK in the presence of the test compound is weaker than an interaction between the prohibitin and the AMPK in the absence of the test compound.

5. The method according to claim 1, comprising using a proximity effect to measure the interaction between the prohibitin and the AMPK.

6. The method according to claim 1, wherein the prohibitin is prohibitin 1.

7. The method according to claim 1, wherein the AMPK is an AMPKβ subunit.

8. The method according to claim 1, wherein the prohibitin is a fusion protein.

9. The method according to claim 1, wherein the AMPK is a fusion protein.

10. A process of making a prohibitin-AMPK complex, comprising:
    isolating a prohibitin overexpressed in a cell or obtained by an in vitro translation system;
    isolating an AMPK overexpressed in a cell or obtained by an in vitro translation system; and
    binding the prohibitin and the AMPK to each other to obtain the prohibitin-AMPK complex.

* * * * *

SEQUENCE LISTING

<160> NUMBER OF SEQ ID NOS: 6

<210> SEQ ID NO 1
<211> LENGTH: 25
<212> TYPE: RNA

```
<213> ORGANISM: Artificial
<220> FEATURE:
<223> OTHER INFORMATION: PHB1 siRNA

<400> SEQUENCE: 1
uuggcaauca gcucagcugc cuugg                                        25

<210> SEQ ID NO 2
<211> LENGTH: 25
<212> TYPE: RNA
<213> ORGANISM: Artificial
<220> FEATURE:
<223> OTHER INFORMATION: PHB1 siRNA

<400> SEQUENCE: 2
ccaaggcagc ugagcugauu gccaa                                        25

<210> SEQ ID NO 3
<211> LENGTH: 25
<212> TYPE: RNA
<213> ORGANISM: Artificial
<220> FEATURE:
<223> OTHER INFORMATION: PHB2 siRNA

<400> SEQUENCE: 3
uacgauucug ugauguggcg aucgu                                        25

<210> SEQ ID NO 4
<211> LENGTH: 25
<212> TYPE: RNA
<213> ORGANISM: Artificial
<220> FEATURE:
<223> OTHER INFORMATION: PHB2 siRNA

<400> SEQUENCE: 4
acgaucgcca caucacagaa ucgua                                        25

<210> SEQ ID NO 5
<211> LENGTH: 9
<212> TYPE: PRT
<213> ORGANISM: Artificial
<220> FEATURE:
<223> OTHER INFORMATION: HA-tag

<400> SEQUENCE: 5

Tyr Pro Tyr Asp Val Pro Asp Tyr Ala
1               5

<210> SEQ ID NO 6
<211> LENGTH: 8
<212> TYPE: PRT
<213> ORGANISM: Artificial
<220> FEATURE:
<223> OTHER INFORMATION: Flag-tag

<400> SEQUENCE: 6

Asp Tyr Lys Asp Asp Asp Asp Lys
1               5
```